(12) United States Patent
Perkins

(10) Patent No.: US 6,441,192 B1
(45) Date of Patent: Aug. 27, 2002

(54) ACYLATION PROCESS

(75) Inventor: Jolyon Francis Perkins, Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/669,318

(22) Filed: Sep. 25, 2000

(30) Foreign Application Priority Data

Oct. 1, 1999 (GB) .............................................. 9923314

(51) Int. Cl.⁷ ...................... C07D 209/12; C07D 403/06
(52) U.S. Cl. ........................................ 548/468; 548/493
(58) Field of Search ................................ 548/493, 468

(56) References Cited

U.S. PATENT DOCUMENTS

| | | | |
|---|---|---|---|
| 5,545,644 A | 8/1996 | Macor et al. | 514/323 |
| 5,559,129 A | 9/1996 | Macor et al. | 514/323 |
| 5,559,246 A | 9/1996 | Macor | 548/468 |
| 5,578,612 A | 11/1996 | Macor et al. | 514/323 |
| 5,607,951 A | 3/1997 | Macor et al. | 514/323 |
| 5,639,779 A * | 6/1997 | Wythes et al. | 514/414 |
| 6,110,940 A | 8/2000 | Harding et al. | 514/323 |
| 6,166,025 A | 12/2000 | Harding et al. | 514/264 |

FOREIGN PATENT DOCUMENTS

| | | | |
|---|---|---|---|
| WO | WO9206973 | 4/1992 | C07D/403/06 |
| WO | WO9606842 | 3/1996 | C07D/403/06 |
| WO | WO9827089 | 6/1998 | C07D/403/06 |
| WO | WO9901135 | 1/1999 | A61K/31/52 |

* cited by examiner

*Primary Examiner*—Robert W. Ramsuer
*Assistant Examiner*—Sonya Wright
(74) *Attorney, Agent, or Firm*—P. C. Richardson; P. H. Ginsburg; A. D. Joran

(57) ABSTRACT

The present invention is concerned with the acylation of indoles, specifically the preparation of 3-acylated indoles which may be further treated to provide indoles having an alternative substituent at the 3-position.

5 Claims, No Drawings

ACYLATION PROCESS

The application claims the benefit of U.K. patent application No. 9923314.0, filed Oct. 1, 1999.

The present invention is concerned with the acylation of indoles, specifically the preparation of 3-acylated indoles which may be further treated to provide indoles having an alternative substituent at the 3-position.

To date, the 3-acylation of indoles has typically been carried out by the method described, for example, in International Patent Application PCT/US91/07194, that is, by reacting a magnesium salt of the indole with an acid chloride:

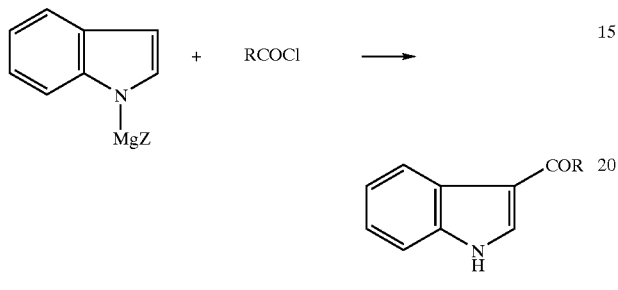

wherein Z is halogen and R is, for example, substituted pyrrolidinyl, azetidinyl, or piperidinyl.

The magnesium salt is prepared by reacting the appropriate indole with an alkyl or aryl magnesium halide, preferably ethyl magnesium bromide, in an inert solvent, for example, diethyl ether or tetrahydrofuran, at a temperature between −30° C. and 65° C., preferably about 25° C.

The acid chloride is prepared by reacting the corresponding acid with, for example, oxalyl or thionyl chloride, in an inert solvent, for example, methylene chloride, diethyl ether or tetrahydrofuran, at a temperature between −10° C. and 25° C. Acids having an N-containing heterocyclic moiety may protect same from the resulting acid chloride by N-substitution with a suitable protecting group, for example, carboxybenzyl (CBZ).

A solution of the acid chloride is then added slowly to a stirred solution of the magnesium salt at a temperature between −30° C. and 50° C., preferably about 25° C., to give the desired 3-acylated indole.

This process for the preparation of 3-acylated indoles, requiring as it does the independent preparation of each starting material, is both time- and labour-intensive and does not lend itself readily to commercial scale-up.

We have therefore developed a new methodology for the preparation of 3-acylated indoles which eliminates the need for independent preparation of the aforementioned starting materials. According to the present invention, 3-acylated indoles may be obtained in good yield by adding solutions of the acid chloride (N-protected if necessary) and the alkyl or aryl magnesium halide separately and simultaneously to a solution of the indole at 'synchronised' rates of molar addition.

Thus the problem addressed by the present invention is to provide a quick and cost effective method for preparing 3-acylated indoles which avoids the unsatisfactory convergent synthesis of the prior art, particularly the necessity to prepare and isolate the magnesium salt of the indole.

As a further cost-saving measure, the process of the present invention requires only one molar equivalent of the expensive indole starting material. This contrasts with the two equivalents required by the prior art process and effectively doubles the yield of acylated material based on indole starting material.

According to the present invention, there is provided a method for the preparation of 3-acylated indoles which involves preparing the acid chloride as described and then adding solutions of (i) the acid chloride and (ii) an alkyl or aryl magnesium halide separately and simultaneously to a stirred solution of the indole in such a way that (a) the two streams of incoming reagents do not come into immediate contact, i.e. they are added some distance apart to prevent their reacting with one another rather than with the indole, and (b) the two reagents are added at 'synchronised' rates of molar addition.

Specifically, the invention provides a process for the preparation of a compound of formula (I)

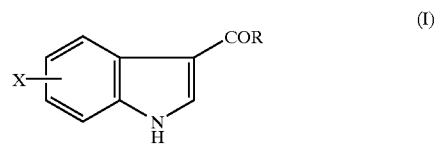

wherein R=$C_1$–$C_6$ alkyl, $C_1$–$C_6$ alkoxy, $C_3$–$C_7$ cycloalkyl, aryl optionally substituted by one or more of hydroxy, $C_1$–$C_4$ alkyl, $C_1$–$C_4$ alkoxy, fluoro, fluoro($C_1$–$C_4$)alkyl and fluoro($C_1$–$C_4$)alkoxy, or N-carboxybenzyl-2-pyrrolidinyl and X is hydrogen or one or more substituents independently selected from cyano, halogen, nitro, $C_1$–$C_6$ alkyl, $C_1$–$C_6$ alkoxy, $C_3$–$C_7$ cycloalkyl and aryl optionally substituted by one or more of cyano, halogen, nitro, $C_1$–$C_4$ alkyl, $C_1$–$C_4$ alkoxy, fluoro($C_1$–$C_4$)alkyl and fluoro($C_1$–$C_4$) alkoxy;

which comprises separately and simultaneously adding to a stirred solution of an indole of formula (II)

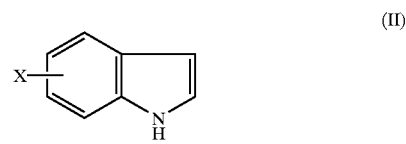

wherein X is as hereinbefore defined;
(i) a solution containing an acid chloride of formula RCOCl wherein R is as hereinbefore defined; and
(ii) a solution containing an alkyl or aryl magnesium halide in such a way that
(a) the solutions (i) and (ii) are added with sufficient separation to prevent their reacting with one another; and
(b) the solutions (i) and (ii) are added at equivalent rates of molar addition.

According to particularly preferred features of the invention, the indole of formula (II) is indole itself or a 5-haloindole and the magnesium halide is an alkyl or aryl magnesium bromide, preferably ethyl magnesium bromide.

The process of the invention is illustrated by the following Examples.

EXAMPLE 1

Preparation of 3-(N-CBZ-2-Pyrrolidinylcarboxy)-5-bromoindole

To a freshly dried vessel equipped with overhead stirring and maintained under a nitrogen blanket was added 5-bromoindole (3.85 kg, 19.6 mol) followed by methylene chloride (12.3L). The resulting mixture was stirred at ambient until an homogeneous solution was obtained, then cooled to 10–12 °C. Solutions of the CBZ-prolinoyl chloride in methylene chloride (20 mol, 1.02 eq) and 1M ethylmagnesium bromide in MTBE (37.7 kg, 39.2 mol, 2 eq) were then added simultaneously over 2–3 hours on opposite sides of the vessel whilst maintaining the temperature at 10–15° C. These additions must be conducted such that the two streams do not mix and that the rates of molar addition of each reagent are continuously synchronised.

The resultant slurry was added to a vigorously stirred mixture of conc. HCl (3L), demineralised water (28L) and THF (29L) over 30 minutes, while maintaining the temperature at below 25° C. The resulting biphasic mixture was stirred for 30 minutes, allowed to settle for 20 minutes, then the phases separated, retaining the upper organic layer. The organic layer was washed with saturated aqueous $NaHCO_3$ (28L) for 20 minutes at 20–25° C., allowed to settle for 20 minutes, then the phases separated, retaining the upper organic layer. The solvents were then removed under reduced pressure while maintaining the temperature at below 50° C.; crystallisation was observed during the later stages. To the resulting slurry was added ethyl acetate (15.5L) and hexane (15.5L) and the resulting mixture cooled to 0° C. and granulated at this temperature for 1 hour. The product was then isolated by filtration, washed with 1:1 hexane:ethyl acetate (10L), then dried overnight in vacuo at 35° C. to yield 6.85 kg (82%) of (R)-3-(N-carboxybenzyl-2-pyrrolidinylcarboxy)-5-bromo-1H-indole as fine white crystals.

Calculated: C=59.03%, H=4.48%, N=6.56% Found: C=59.01%, H=4.50%, N=6.58%

EXAMPLE 2

Preparation of 3-(N-CBZ-2-Pyrrolidinylcarboxy) indole

To a solution of 25 mmol of indole in methylene chloride (25 mL) was simultaneously added over 1 hour a solution of CBZ-prolinoyl chloride (25 mmol) in 25 mL of MTBE and 50 mL of a 1M solution of ethylmagnesium bromide in MTBE. The two streams were added on opposite sides of the vessel with efficient stirring and the temperature maintained at 10–15° C. Upon completion of the additions, the reaction was quenched by addition to 1.0M aqueous HCl (50 mL). After stirring, settling and phase separation, the organic phase was washed with brine (50 mL) and then reduced in volume by 75% causing crystallisation of the product. The product was filtered off, washed with ethyl acetate (~10 mL) and dried in vacuo at 45° C. Yield 81%.

EXAMPLE 3

Preparation of 3-Benzoyl-5-bromoindole

3-Benzoyl-5-bromoindole was obtained in 94% yield using the procedure described in Example 2.

EXAMPLE 4

Preparation of 3-Benzoylindole

3-Benzoylindole was obtained in 91% yield using the procedure described in Example 2.

It will be appreciated by the skilled person that 3-acylated indoles obtained according to the process of the invention may be further treated to give indoles having an alternative substituent at the 3-position.

Thus it is a specific embodiment of the present invention that when R=N-CBZ-2-pyrrolidinyl and X=bromo, the 3-(N-CBZ-2-pyrrolidinylcarboxy)-5-bromoindole of formula (I) so obtained

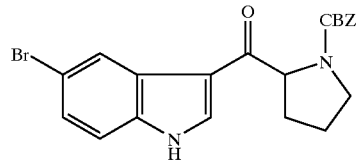

may then be reduced using, for example, lithium aluminium hydride in tetrahydrofuran, to give 3-(N-methyl-2(R)-pyrrolidinylmethyl)-5-bromoindole (III)

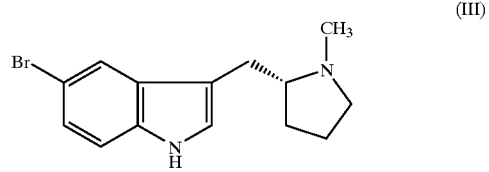

(III)

which in turn may be converted using a suitable Heck reaction to 3-(N-methyl-2(R)-pyrrolidinylmethyl)-5-(2-phenylsulphonylethenyl)-1H-indole (IV)

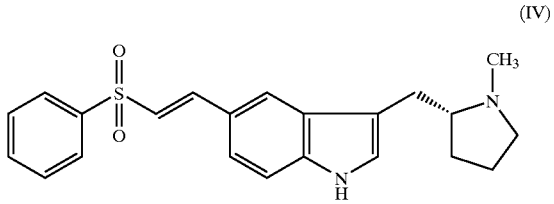

(IV)

which in turn may be catalytically hydrogenated to give 3-(N-methyl-2(R)-pyrrolidinylmethyl)-5-(2-phenylsulphonylethyl)-1H-indole (V):

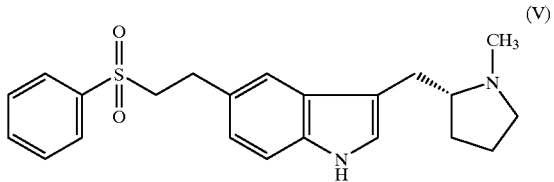

(V)

which compound is a known $5-HT_1$ agonist used in the treatment of migraine.

What is claimed is:

1. A process for the preparation of a compound of formula (I)

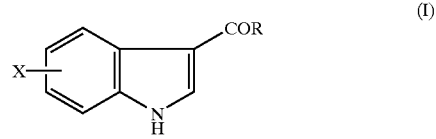

(I)

wherein $R=C_1-C_6$ alkyl, $C_1-C_6$ alkoxy, $C_3-C_7$ cycloalkyl, aryl optionally substituted by one or more of hydroxy, $C_1-C_4$ alkyl, $C_1-C_4$ alkoxy, fluoro, fluoro$(C_1-C_4)$alkyl and fluoro$(C_1-C_4)$alkoxy, or N-carboxybenzyl-2-pyrrolidinyl and X is hydrogen or one or more substituents independently selected from cyano, halogen, nitro, $C_1-C_6$ alkyl, $C_1-C_6$ alkoxy, $C_3-C_7$ cycloalkyl and aryl optionally substituted by one or more of cyano, halogen, nitro, $C_1-C_4$ alkyl, $C_1-C_4$ alkoxy, fluoro$(C_1-C_4)$alkyl and fluoro$(C_1-C_4)$ alkoxy;

which comprises separately and simultaneously adding to a stirred solution of an indole of formula (II)

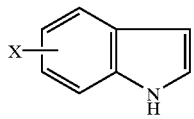
(II)

wherein X is as hereinbefore defined;
- (i) a solution containing an acid chloride of formula RCOCl wherein R is as hereinbefore defined; and
- (ii) a solution containing an alkyl or aryl magnesium halide in such a way that
  - (a) the solutions (i) and (ii) are added with sufficient separation to prevent their reacting with one another; and
  - (b) the solutions (i) and (ii) are added at equivalent rates of molar addition.

2. A process according to claim 1 wherein the indole of formula (II) is indole itself or a 5-haloindole.

3. A process according to claim 1 wherein the magnesium halide is an alkyl or aryl magnesium bromide.

4. A process according to claim 1 wherein the magnesium halide is ethyl magnesium bromide.

5. A process according to claim 1 wherein R is N-CBZ-2-pyrrolidinyl and X is bromo and the compound of formula (I) so obtained is

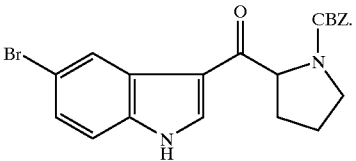

* * * * *